(12) United States Patent
Rodriguez et al.

(10) Patent No.: US 10,369,079 B2
(45) Date of Patent: Aug. 6, 2019

(54) DRUG REFILL APPLICATOR SYSTEM AND METHOD OF USE

(71) Applicants: Andres Rodriguez, Azusa, CA (US); Pedrum Minaie, Burbank, CA (US); Tun Min Soe, Irvine, CA (US); Jason Shih, Yorba Linda, CA (US); Andrew Dunn, Santa Monica, CA (US); Andrew Urazaki, Arcadia, CA (US); Bin Wang, Arcadia, CA (US); Fukang Jiang, Arcadia, CA (US)

(72) Inventors: Andres Rodriguez, Azusa, CA (US); Pedrum Minaie, Burbank, CA (US); Tun Min Soe, Irvine, CA (US); Jason Shih, Yorba Linda, CA (US); Andrew Dunn, Santa Monica, CA (US); Andrew Urazaki, Arcadia, CA (US); Bin Wang, Arcadia, CA (US); Fukang Jiang, Arcadia, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 789 days.

(21) Appl. No.: 14/579,231

(22) Filed: Dec. 22, 2014

(65) Prior Publication Data

US 2015/0174007 A1 Jun. 25, 2015
US 2016/0374901 A9 Dec. 29, 2016

Related U.S. Application Data

(63) Continuation-in-part of application No. 13/419,968, filed on Mar. 14, 2012, now abandoned.
(Continued)

(51) Int. Cl.
*A61J 1/20* (2006.01)
*A61J 1/22* (2006.01)
(Continued)

(52) U.S. Cl.
CPC ............ *A61J 1/22* (2013.01); *A61M 5/14276* (2013.01); *B65B 3/003* (2013.01); *A61J 1/201* (2015.05); *A61M 2005/14268* (2013.01)

(58) Field of Classification Search
CPC .................. A61J 1/22; A61M 5/14276; A61M 2005/14268; B65B 3/003
(Continued)

(56) References Cited

U.S. PATENT DOCUMENTS

2004/0176732 A1* 9/2004 Frazier .............. A61M 37/0015
604/345
2007/0123843 A1 5/2007 Gill
(Continued)

FOREIGN PATENT DOCUMENTS

JP          2003-47656 A      2/2003
WO     WO 2009137777     * 11/2009

OTHER PUBLICATIONS

PCT International Patent Application No. PCT/US2014/071917, International Search Report and Written Opinion dated Apr. 24, 2015, 13 pages.

*Primary Examiner* — Timothy L Maust
*Assistant Examiner* — James R Hakomaki
(74) *Attorney, Agent, or Firm* — Morgan, Lewis & Bockius LLP

(57) ABSTRACT

Embodiments of the present invention involve a refill apparatus comprising at least one pump, a plurality of reservoirs, a plurality of reservoir fluid channels each associated with one of the reservoirs, a plurality of valves, each having a cracking pressure, for fluidically sealing the reservoir fluid channels and the outlet fluid channel, an outlet fluid channel fluidically connected to the reservoir fluid channels, and a needle having a lumen in fluid communication with the outlet fluid channel. A parameter such as a pressure level is monitored, and one or more pumps and various ones of the
(Continued)

valves are actuated in accordance with a protocol comprising a sequence of steps whereby fluidic pathways are opened between different ones of the reservoirs and the needle in a washing and filling sequence, each of the steps being associated with an expected pressure level.

19 Claims, 10 Drawing Sheets

Related U.S. Application Data

(60) Provisional application No. 61/920,195, filed on Dec. 23, 2013, provisional application No. 61/452,399, filed on Mar. 14, 2011.

(51) Int. Cl.
*B65B 3/00* (2006.01)
*A61M 5/142* (2006.01)

(58) Field of Classification Search
USPC .............................................................. 141/2
See application file for complete search history.

(56) References Cited

U.S. PATENT DOCUMENTS

| 2008/0172043 | A1 | 7/2008 | Sheppard et al. |
| 2013/0186474 | A1 | 7/2013 | Chong et al. |
| 2013/0276974 | A1 | 10/2013 | Pang et al. |

\* cited by examiner

DETACHABLE
31 Ga NEEDLE

MODULAR UNIT

SYSTEM DIAGRAM OF A REFILL SYSTEM EMBODIMENT

SYSTEM DIAGRAM OF AN ALTERNATIVE REFILL SYSTEM EMBODIMENT WITH MULTIPLE DRUG RESERVOIRS

SYSTEM DIAGRAM OF AN ALTERNATIVE REFILL SYSTEM EMBODIMENT WITH A RINSE RESERVOIR

IMPLANT EXAMPLE 1

GRAPH DISPLAYING THE PRESSURE FLUCTUATION OVER THE REFILL PHASE INCLUDING SPECIFIC PRESSURE TRIGGER POINTS: 1. START VACUUM, 2. DRUG CHAMBER EMPTY, 3. START FILLING W/WASH SOLUTION, 4. DRUG CHAMBER FULL, 5. END OF FIRST WASH CYCLE, 6. START FILLING WITH DRUG, 7. END OF FILLING PROCESS

REFILL CYCLE PRESSURE CURVES REPRODUCED AT VARYING PRESSURES

FIG. 10 ASPIRATION BASED ON PRESSURE READINGS

DRUG REFILL APPLICATOR SYSTEM AND METHOD OF USE

RELATED APPLICATIONS

This application a continuation-in-part of U.S. patent application Ser. No. 13/419,968, filed Mar. 14, 2012, which claims the benefit of U.S. Provisional Patent Application No. 61/452,399, filed Mar. 14, 2011, and also claims the benefit of U.S. Provisional Patent Application No. 61/920,195, filed Dec. 23, 2013, the entire disclosure of each of which is hereby incorporated herein by reference.

BACKGROUND

Medical treatment often requires the administration of a therapeutic agent (e.g., medicament, drugs, etc.) to a particular part of a patient's body. As patients live longer and are diagnosed with chronic and/or debilitating ailments, the need to place even more protein therapeutics, small-molecule drugs, and other medications into targeted anatomical areas will only increase. Some maladies, however, are difficult to treat with currently available therapies and/or require administration of drugs to difficult-to-reach anatomical regions. Many of these therapies would benefit from concentrated target-area treatment, which would reduce systemic side effects. Furthermore, certain drugs such as protein therapeutics are expensive, costing thousands of dollar per vial. For these reasons, new and improved approaches to targeted drug delivery are constantly sought.

Implantable drug-delivery devices with refillable drug reservoirs address and overcome many of the problems associated with conventional drug-delivery modalities. They generally facilitate controlled delivery of pharmaceutical solutions to a specified target. As the contents of the drug reservoir deplete, a clinician may refill the reservoir in situ, i.e., while leaving the device implanted within the patient's body.

As implantable devices of varying sizes, refill requirements, and implant locations become available, the refill process becomes progressively complicated. However, the refill systems themselves and the associated processes have not fundamentally improved. Current refill systems may use intricate systems of syringes, multiple three-way valves, pinch valves, etc. that are manually or electronically actuated to transition from open to closed positions throughout the refill process. These systems have a learning curve and multiple steps that are prone to human or programming error. Additionally, if refill is performed manually, improper or sub-optimal needle insertion may cause damage to the drug-delivery device, additional patient discomfort or, worse, danger to the patient.

Therefore, ways of simplifying the procedure and reducing the number of potential errors is highly desired.

SUMMARY

In various embodiments, the present invention relates to refill systems incorporating a refill needle, reservoirs, a system of passive check valves of known cracking pressures, a pressure actuation pump used to refill drug pump devices, and various sensors throughout the system. By automating portions of the system, implementations of the present invention allow the clinician to concentrate on the overall refill procedure without the distractions of actuating each step of a refill sequence.

The present invention provides, in various embodiments, a refill system for drug-delivery devices. For example, the invention may be implemented as a system for refilling an implanted, refillable drug pump device including a drug reservoir with a fill port. The system may include a needle for insertion into the fill port of the drug pump device and fluidically connectable to one or more fluid containers, one or more pumps for causing fluid flow through the needle between the fluid container(s) and the drug reservoir within the device being refilled, a plurality of check valves, electronic circuitry including a processor for controlling operation of the pump(s), and a wireless communication module facilitating wireless data exchange between the refill system and the implanted drug pump device. The system may further include tubing for fluidically connecting the fluid container(s) to the needle. This refill system may also be used to refill subcutaneous pumps that are placed externally (e.g., wearable insulin pumps and pain pumps).

Embodiments of the present invention provide a partially to fully automated system with multiple built-in safeguards that reduce the number of steps and the subsequent total time of the refill process. Passive mechanical safeguards prevent errors, and various structural features and configurations may minimize the dead space in tubing sets, thereby reducing or eliminating drug waste during administration. In some embodiments, pressure and/or other parameters are monitored and detection of pre-set values triggers the initiation and completion of one or more (or all) steps in the refill process.

The present invention simplifies the refill process and provides many advantages. Unlike current refill systems that use intricate systems of syringes, multiple three-way valves, pinch valves, etc. that are manually or electronically changed from open to closed positions throughout the refill process, embodiments of the present invention rely on the known pressures required throughout the refill process to partially or fully automate the refill procedure.

Accordingly, in a first aspect, embodiments of the invention feature an apparatus for refilling a reservoir that includes or consists essentially of a plurality of reservoirs, a plurality of reservoir fluid channels, an outlet fluid channel, a plurality of valves for fluidically sealing the reservoir fluid channels and the outlet fluid channel, at least one sensor, at least one actuation mechanism, a needle, and a controller. Each of the plurality of reservoir fluid channels is associated with one of the reservoirs. The outlet fluid channel is fluidically connected to the reservoir fluid channels. Each of the plurality of valves has a cracking pressure. The at least one sensor monitors pressure in the reservoir fluid channels and the outlet fluid channel. The needle has a lumen in fluid communication with the outlet fluid channel, and the needle is configured for insertion into a drug-delivery port of an implantable medical device. The controller actuates at least one said pump and various ones of the valves in accordance with a protocol including or consisting essentially of a sequence of steps, whereby fluidic pathways are opened between different ones of the reservoirs and the needle in a washing and filling sequence, each of the steps being associated with an expected pressure level.

Embodiments of the invention may include one or more of the following in any of a variety of combinations. The controller may be configured to execute a step in the sequence upon detection, via the sensor, of the expected pressure level. At least some of the valves may be active valves. At least some of the valves may be passive valves. The apparatus may include at least one flow sensor and/or at least one biosensor. The controller may be configured to control the pump so as to maintain a pressure through the outlet lumen below a pressure causing damage to an implantable device (e.g., an implantable medical device) connected to the needle. The controller may be configured to control the pump so as to maintain a pressure through the outlet lumen below a pressure causing an implantable device (e.g., an implantable medical device) connected to the needle to expel material. The controller may be configured to control the pump so as to maintain, during a filling or aspiration step, a pressure through the outlet lumen above a cracking pressure of check valves in the fluid lines operatively used during the filling or aspiration step. The controller may include a memory for storing a plurality of expected pressure levels and expected intervals therebetween. The controller may be configured to monitor the at least one pressure sensor and, upon detection of an expected pressure level following an expected interval, to initiate or terminate a protocol step. The apparatus may include at least one sensor for a parameter other than pressure, and the controller (i) may include a memory for storing a temporal profile of expected parameter values including pressure values and (ii) may be configured to monitor the sensors and, upon detection of a deviation from the stored profile, report an error condition. The parameter values may include or consist essentially of a detected flow rate, cumulative flow, pressure slope change, duration of a specific pressure, and/or plateauing within specific pressure ranges.

In a second aspect, embodiments of the invention feature a method of refilling an implantable device having a drug chamber. A refill apparatus is provided. The refill apparatus includes or consists essentially of at least one pump, a plurality of reservoirs, a plurality of reservoir fluid channels each associated with one of the reservoirs, a plurality of valves, each having a cracking pressure, for fluidically sealing the reservoir fluid channels and the outlet fluid channel, an outlet fluid channel fluidically connected to the reservoir fluid channels, and a needle having a lumen in fluid communication with the outlet fluid channel. A pressure level is monitored. The needle is inserted into a drug-delivery port of the implantable device. At least one said pump and various ones of the valves are actuated in accordance with a protocol including or consisting essentially of a sequence of steps whereby fluidic pathways are opened between different ones of the reservoirs and the needle in a washing and filling sequence, each of the steps being associated with an expected pressure level.

Embodiments of the invention may include one or more of the following in any of a variety of combinations. The washing and filling sequence may include or consist essentially of flushing a drug chamber of the implantable device by (i) causing a first fluid from a first one of the reservoirs to enter the drug chamber via the needle at a pressure not exceeding a maximum tolerable pressure, (ii) removing the first fluid from the drug chamber, and (iii) causing a drug-containing liquid to enter at a pressure not exceeding the maximum tolerable pressure. The maximum tolerable pressure may be less than a pressure causing damage to the implantable device. The maximum tolerable pressure may be less than a pressure causing flow through the implantable device. At least one parameter other than pressure may be monitored, and, upon detection of a parameter value matching a stored trigger value, a step in the sequence may be initiated or terminated. The trigger values may include or consist essentially of a detected flow rate, cumulative flow, pressure slope change, duration of a specific pressure, and/or plateauing within specific pressure ranges. At least one parameter other than and in addition to pressure may be monitored. A temporal profile of expected parameter values including pressure values may be stored. Based on the monitored parameters, an error condition may be reported upon detection of a deviation from the stored profile.

The term "substantially" or "approximately" means±10% (e.g., by weight or by volume), and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1A:
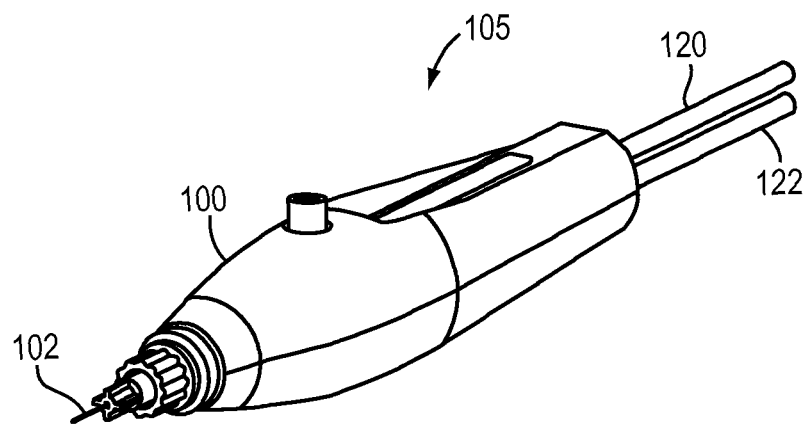
FIG. 1A is a perspective view of a handheld refill tool in accordance with various embodiments of the invention.
Figure 1B:
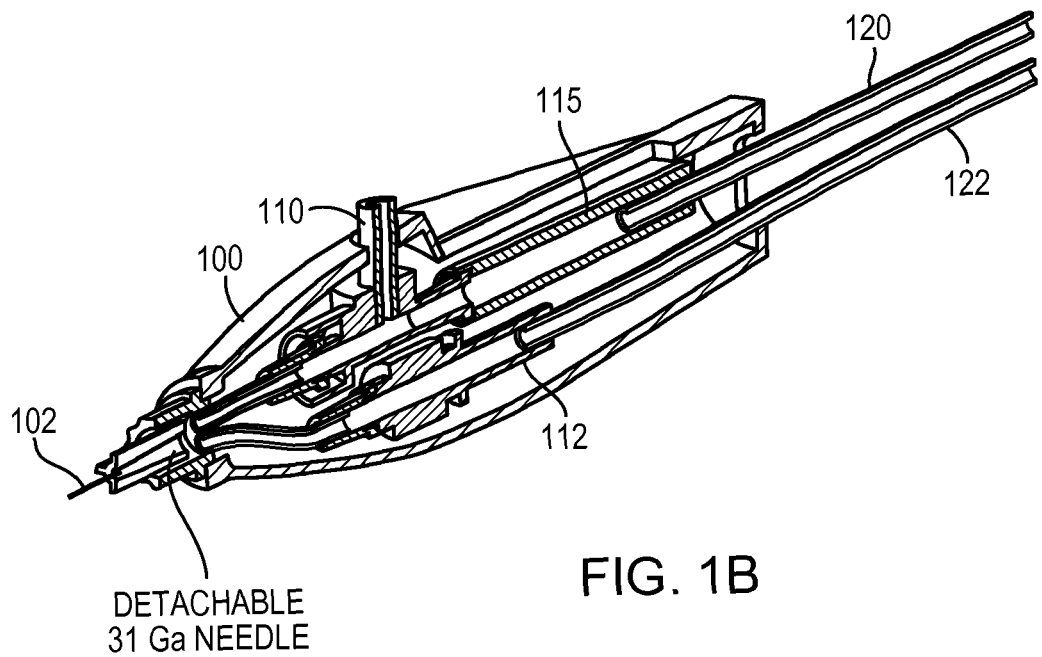
FIG. 1B is a cutaway view of the device shown in FIG. 1A.

The present invention relates, generally, to refill systems for implantable drug pump devices with refillable drug reservoirs, e.g., ocular drug pumps, implantable insulin pumps, inner ear pumps, and brain pumps. With reference to FIGS. 1A and 1B, the refill system may be implemented in multiple components, one of which is a handpiece 100. As described in greater detail below, the pumps, control circuitry, and some of the valves and sensors are integrated into a reusable base unit, a pair of fluid channels from which enter the distal end the handpiece 100; the handpiece terminates in a detachable (and replaceable) refill needle 102, which is preferably a small-bore needle. The handpiece 100 includes an ergonomic handle portion 105 that allows a clinician to refill the implanted device in situ. In preferred embodiments, the same needle 102 is used during the entire refill process so as to minimize the needle insertion frequency into the drug reservoir and the associated stress for patient and clinician, as well as the wear on the refill port. A single needle insertion may suffice even if multiple fluids (e.g., multiple separately stored drugs to be administered together) are to be injected into the drug pump device as explained below. The needle 102 is, thus, sequentially connected to different fluid containers.

The handpiece 100 is desirably weight-balanced and may have built-in transparent windows so fluid movement can be visually confirmed. For safety purposes, the handpiece 100 may have a built-in, user-actuated retractable needle-storage slot to conceal and store the needle 102 when the refill tool is not in use. In certain embodiments, as best seen in the cutaway view of FIG. 1B, the handpiece 100 may contain a pair of check valves 110, 112 and a drug reservoir 115. Either or both check valves 110, 112 may be active or passive to help regulate the fluid fill and extraction processes. In the illustrated embodiment, the valve 110 is a two-way check valve and the valve 112 is a one-way check valve. The valves 110, 112 are fluidically coupled to fluid lines 120, 122, respectively. The handpiece 100 may also contain one or more modalities to assist in detecting the refill port of the device to be refilled. Such modalities may include a pressure sensor, a light source, a capacitive sensing or piezo-element tip, and/or a magnetic or Hall effect structure, which may provide the user with additional feedback throughout the refill process.

Figure 2:
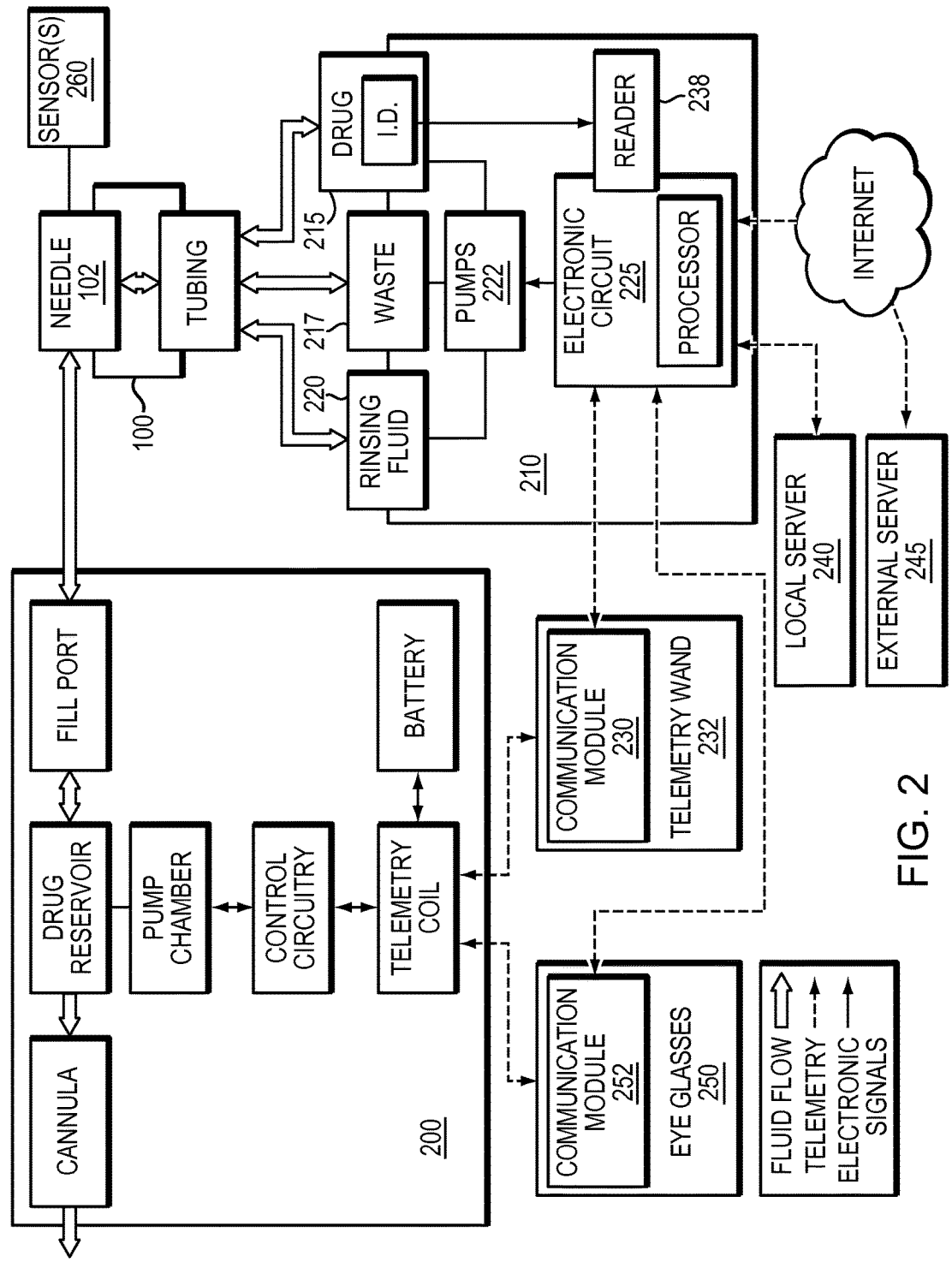
FIG. 2 is a block diagram of a drug pump device and refill system in accordance with various embodiments of the invention, illustrating communication links between various components of the system.

FIG. 2 illustrates the operating environment and general system configuration of a representative refill system implementing the present invention. As described, for example, in U.S. Ser. No. 13/632,722, the entire disclosure of which is hereby incorporated by reference, a refillable drug-pump device 200 may include a drug reservoir, a pump chamber and control circuitry for operating the device 200. Drug from the reservoir is delivered to an anatomical site via a cannula, and the reservoir may be refilled by the needle 102 of the handpiece 100 via a fill port. As described below, various operative components of the refill system are housed in a base unit 210, which contains a drug refill reservoir 215, a waste reservoir 217, and a reservoir 220 for rinsing fluid. A pumping unit 222 includes one or more pumps, e.g., one or more pneumatic air pumps, vacuum pumps, combination dual-diaphragm pumps, or any other pump configurations known in the field to create a suitable pressure differential. Further, it is well known and common practice in the medical industry to create a sterile barrier between any liquid and the pump itself by using sterile filters and an air gap. This allows the pumping unit 222 to be modular and reusable. The pumping unit 222 may comprise more than one pump according to the requirements of the refill process such as the number of fluids, fluidic channels, and pump-actuation requirements.

In various embodiments, these pumping units are regulated by software operative within an electronic control circuit 225 that includes a microprocessor. However, the clinician may opt to manually trigger the start of each phase of the refill procedure using a mechanical actuator after the previous phase has ended. The actuator may be built into the handpiece 100, but some buttons or switches may be located separately such as in a foot pedal. If the drug-delivery device contains one or more sensors (flow, pressure, biologic, etc.), the pumping unit 222 may actively communicate with the device 200 through telemetry or other electronic communication methods to ensure successful refill and no accidental drug delivery during the refill process. Such communication protocols may also be used during refill to run diagnostic checks on the drug-delivery device. Flow rates and/or pressure readings known to be accurate may be compared to sensor readings from the device 200 to calibrate a flow sensor via a known dosing profile and/or a pressure sensor via sensed pressure fluctuations during the refill process. Such diagnostic and recalibration protocols improve the accuracy of drug delivery over the course of the lifetime of the device 200.

Thus, the control circuitry 225 of the base unit 210 may include a communication or telemetry module (including a transceiver and related circuitry) 230 provided separately from the control circuitry 225, e.g., in a handheld telemetry wand 232 that allows the clinician to conveniently bring the wand 232 in the vicinity of the implanted pump device 200. The wand may be corded to the base unit 210, or may communicate with the base unit 210 via a separate wireless connection. If employed, the wand 232 may be used to interrogate the device 200 and allows for bi-directional data exchange and/or power transfer. Interrogation may involve, for example, switching the device 200 to a refill mode in which the device's internal actuation (electrolysis, electroosmosis, piezo-electric actuation, etc.) is turned off, and information such as refill drug name (e.g., the ID associated with a removable drug reservoir 215 and read by a reader 238), concentration, and volume may be transmitted to the device 200. The interrogation step may also include an authentication protocol to prevent drug off-label use and to ensure the implant's software security.

The data exchanged with the drug pump device 200 may be stored on a local server 240 integrated with or connected to the base unit 210. Alternatively, the communication module 230 may permit the base unit 210 to communicate with an external server 245, e.g., remotely via the Internet. For example, the base unit 210 may have Wi-Fi, Zigbee, or a cellular phone chip (GSM, CDMA) that is constantly activated to cellular service or other wireless capability. This permits patient and drug data to be stored outside the refill system ("in the cloud"), and may provide further levels of security and operational flexibility.

In some embodiments, special eyeglasses 250 equipped with a telemetry module 252 are used to recharge the battery of the device 200; such eyeglasses are described in U.S. Ser. No. 12/463,251, filed on May 8, 2009, the entire disclosure of which is hereby incorporated by reference. These eyeglasses 250 and the base unit 210 of the refill system may be connected to each other or to a common console, and wireless data exchange with the drug pump device 200 may occur via the eyeglasses rather than a separate telemetry wand 232.

In some embodiments, one or more sensors are placed strategically in the refill system for continuous monitoring and detection of phase completion. In one embodiment, a pressure sensor 260 in the needle tip 102 is used primarily to detect the pressure in the drug reservoir of the device 200 and trigger the initiation and completion of each step of the refill process as described below. The pressure sensor 260 in combination with passive check valves may be used to fully automate the process. The pressure sensor 260 in the needle tip 102 may also detect improper insertion (e.g., midway through a septum) of the refill needle 102 into the fill port of the device 200. Pressure sensors may be deployed in the drug reservoir 215 and waste reservoir 217 to detect possible occlusions in the system, triggering shutdown of the refill process. In some embodiments, a pressure sensor is located within the fluidic path between the pumping unit 222 and the reservoirs 215, 217 to detect faults such as fluidic path leaks.

Flow sensors may be placed inline or around the fluidic paths to monitor the flow of drug refill or waste extraction. In some implementations, these flow sensors are merely structural components such as flexible flaps that have different orientations according to the fluid-flow direction and/or rate. This provides the clinician with a visual verification of flow. In other embodiments, flow sensors utilize time-of-flight, thermal effects, chemical concentration, and/or pressure to provide accurate continuous flow-rate measurements, from which total volumes of wash insertion, wash extraction, and drug refill can be calculated. Other ways of metering fluid volumes delivered and extracted may be used as well.

Implantable devices are vulnerable to tissue ingrowth and possible infection. Accordingly, the refill needle 102 may contain a biosensor (also indicated at 260) to detect specific conditions such as inflammatory biomarkers, bacterial infection, etc. Additionally, if the waste reservoir 217 is separate and removable, additional tests may be performed on the extracted waste fluid using external equipment such as lab assays and a mass spectrometer.

Figure 3:
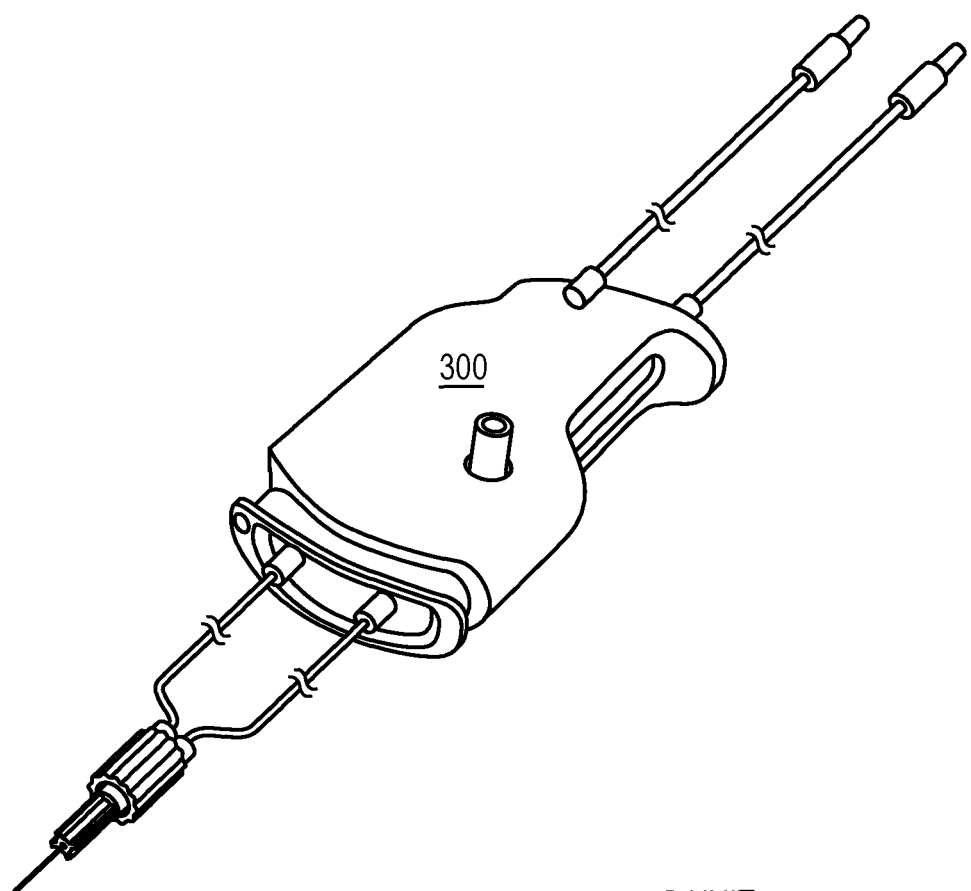
FIG. 3 is a perspective view of a modular unit in accordance with embodiments of the invention.

A representative modular unit 300 is shown in FIG. 3. Besides the reservoirs, the modular unit 300 may include features such as windows through which waste extraction and drug refill can be visualized during the refill process. The waste reservoir 217 may be coated so the introduction of liquid will give the reservoir a characteristic (e.g., noxious) coloring. Each reservoir may also have different types of connection so that the reservoirs are not mistakenly interchanged. The modular unit 300 may also include structural features such as tubing management and safe needle storage, as well as slots that accommodate standard drug vials that may serve as the reservoirs (obviating the need to fill the drug reservoir 215 with a syringe). The modular unit 300 may be placed in the sterile field so the clinician may visually monitor the progress of the refill process through the windows. Depending on the refill requirements (refill drug volume, number of wash cycles, etc.), the modular unit 300 may be built into the handpiece 100.

The modular unit 300 may incorporate multiple drug reservoirs. In one embodiment, the modular unit 300 contains two drug reservoirs 215 and an additional mixing reservoir (not shown). Inactive drug from one drug reservoir and an activating agent from the second drug reservoir, for example, may be transferred into the mixing reservoir where the drug is activated and readied for injection. Other configurations incorporating a plurality of reservoirs actuated in parallel or successive steps, or in any combination, are also possible. In some such embodiments, electronic regulators and/or active valves may be utilized to selectively close certain fluidic paths at certain time periods. The modular unit 300 may also contain a heating element for warming the drug to body temperature, e.g., to reduce patient discomfort caused by the temperature difference during introduction of the drug.

Figure 4:
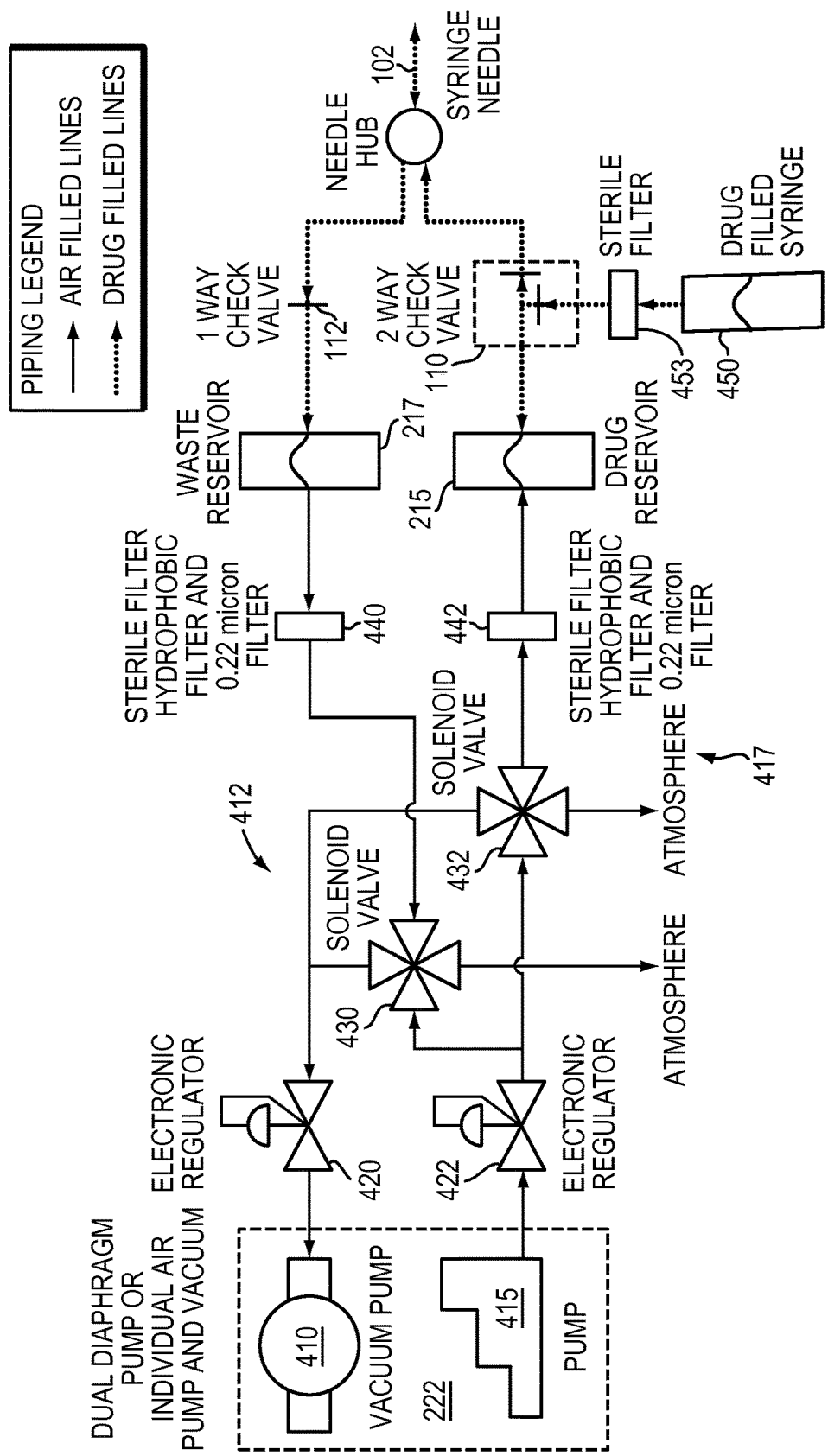
FIGS. 4-6 are piping diagrams in accordance with various embodiments of the invention.
Figure 5:
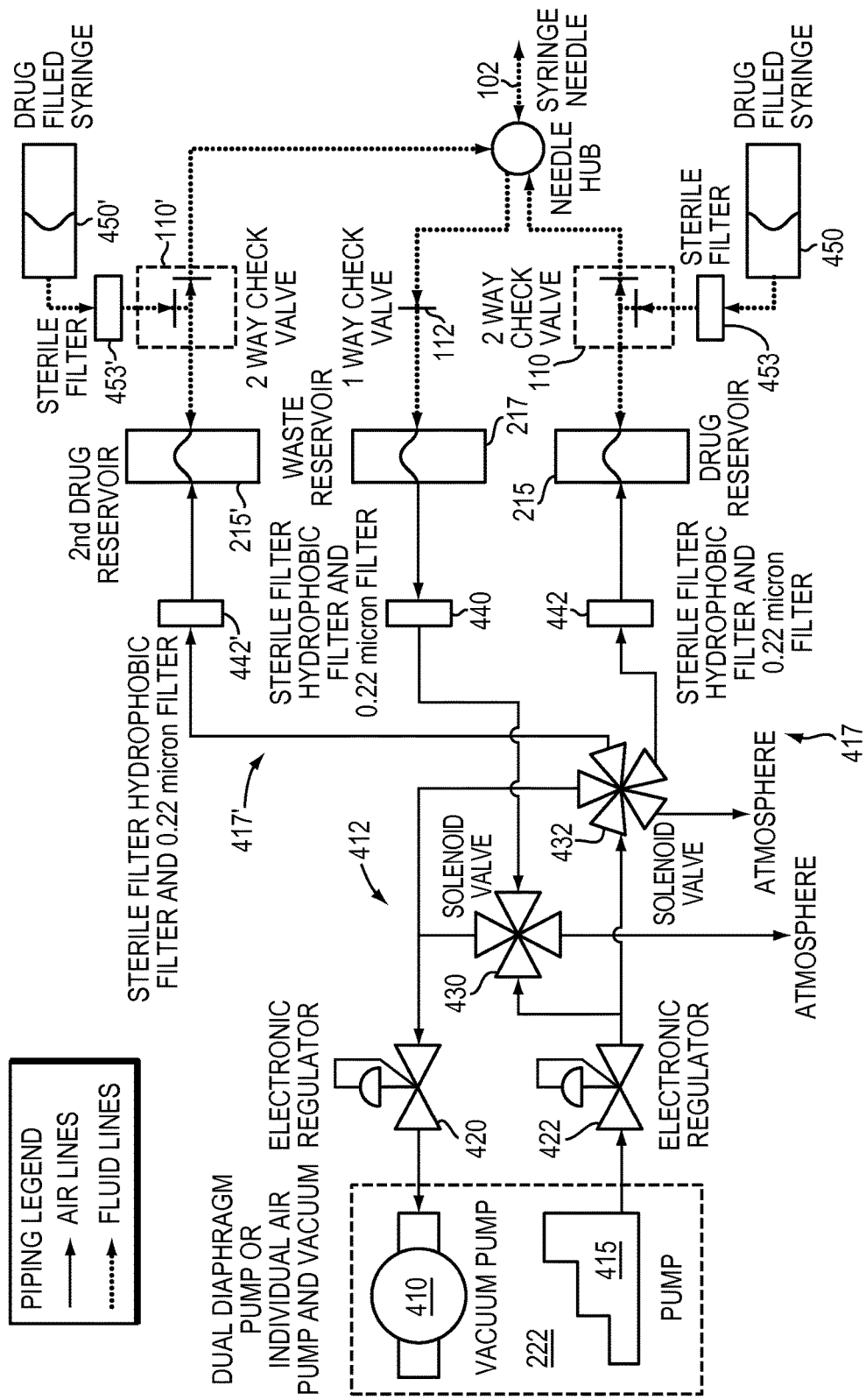
Figure 6:
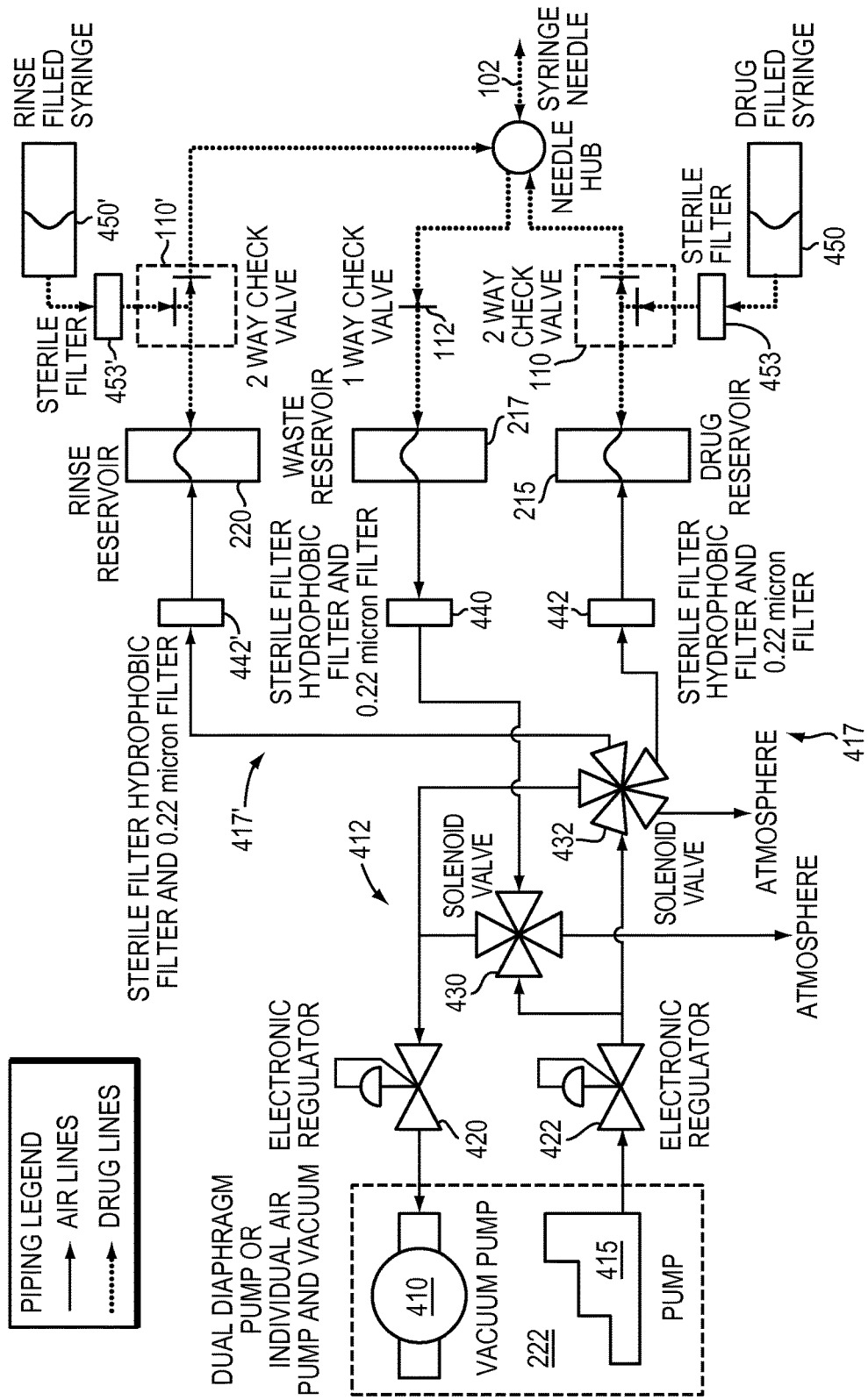

Representative fluidic arrangements for refill systems in accordance herewith are shown in FIGS. 4-6. In the embodiment depicted in FIG. 4, the pumping unit 222 includes a vacuum pump 410 for drawing material from the waste reservoir 217 over a fluid line 412 and a pump 415 that drives liquid drug from the drug reservoir 215 through the needle 102 via a fluid line 417. The pump 415 may be a standard mechanical pump (e.g., gear, diaphragm, peristaltic, etc.). A pair of electronic regulators 420, 422 control the operation of the pumps 410, 415, and are themselves under the control of the electronic control circuitry 225 shown in FIG. 2. A pair of solenoid valves 430, 432, also under the control of the regulators 420, 422 and/or circuitry 225, allow the fluid lines 412, 417 to be vented to atmosphere. The fluidic arrangement also includes a pair of inline sterile filters 440, 442. As explained above, the various illustrated components may be as desired in the handpiece 100, the base unit 210, and the modular unit 300. The drug reservoir 215 is filled by a syringe 450 via the two-way check valve 110 after passing through a sterile filter 453.

FIG. 5 illustrates an alternative fluidic arrangement that includes an additional drug reservoir 215' and associated components (i.e., check valve 110', sterile filters 442', 453' and syringe 450'). These components are fluidically connected to the pump 415 over a third fluid line 417'. The pump 415 alternately controls flow over and venting of one of the lines 417, 417' by means of an expanded solenoid valve 432, so that drug in either of the reservoirs 215, 215' may be selectably expelled through the needle 102.

FIG. 6 illustrates a fluidic arrangement containing a rinse reservoir 220. The piping is identical to that shown in FIG. 5, with output flow from the rinse reservoir 220 under the control of the pump 415.

The refill system may include features that minimize dead space, thereby reducing the amount of drug required for the refill process. This reduces the total cost per procedure. In one embodiment, the drug refill reservoir 215 is placed in the handpiece 100 so that drug is not wasted in the tubing between the needle tip 102 and the reservoir 215. This configuration is useful in cases where the refill volume does not hinder the user's ability to hold and properly use the refill handpiece 100. In another configuration, a modular unit is placed within the sterile field, and contains the drug and waste reservoirs 215, 217, thereby reducing the fluid-containing tubing length compared to placement of the drug reservoir in the pumping unit outside of the sterile field.

The drug refill systems described above may be used to fill, flush, or extract material from a reservoir. Techniques for using the systems will now be discussed.

Preparation Phase

With reference to FIGS. 4-6, a preparation phase is conducted within the sterile field, and begins with filling a syringe 450 with medicament. Air is purged from the syringe 450, which is then connected to the refill handpiece 100 or modular unit 300 via a secure connection (e.g., a luer lock connection). The syringe contents are transferred through a sterile barrier 453, through the two-way check valve 110, and into the refill drug reservoir 215. The solenoid valve 432 is initially open to the atmosphere and the passive two-way check valve 110 is open to the drug reservoir. Therefore, the drug from the syringe 450 is biased only to enter the drug reservoir 215. This step may be repeated for any additional drug or wash solutions necessary in adjacent reservoirs 215'. The two-way check valves 110, 110' may have different diameters to prevent the connection of the wrong needle. Alternatively, the medicament vials may be replaceable components integrated into the modular unit 300 to obviate the need for a syringe 450.

Drug Refill Step (Aspiration and Fill Cycles)

Figure 7:
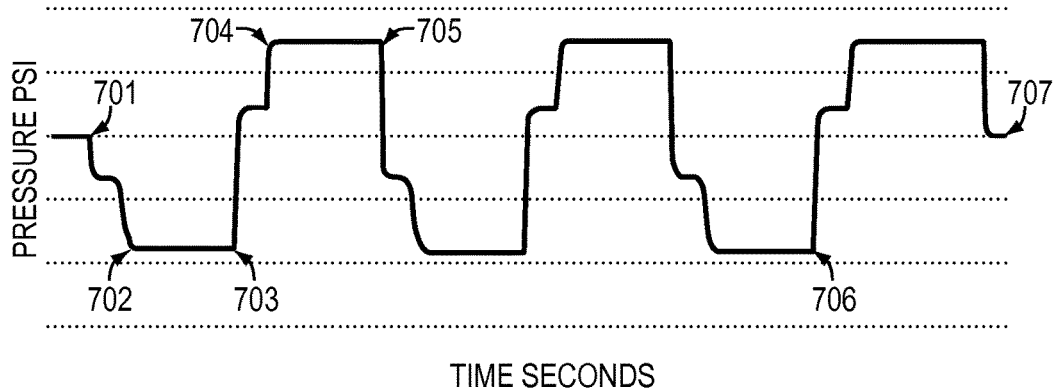
FIG. 7 is a graph illustrating the pressure-time profile of a representative aspiration and fill sequence.
Figure 8:
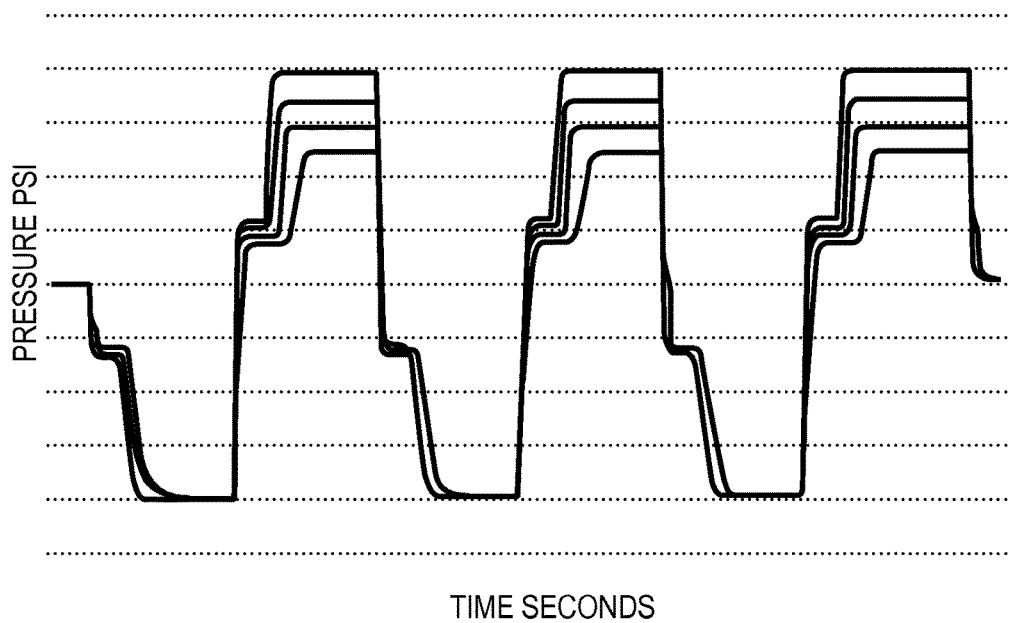
FIG. 8 depicts retention of the basic curve profile shown in FIG. 7 using different fill and vacuum pressures.
Figure 9:
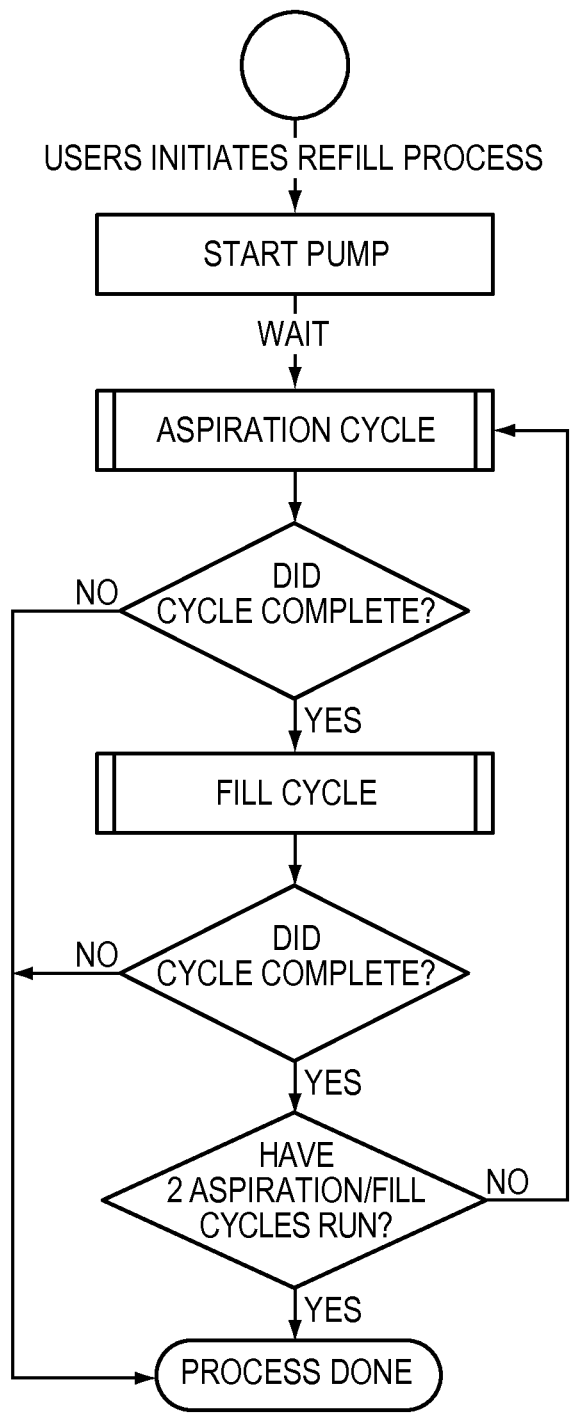
FIG. 9 is a flowchart illustrating a basic decision tree for a refill cycle in accordance with embodiments of the invention.

With reference to FIG. 2, drug refill may be initiated by the insertion of the needle 102 into the refill port of the medical device 200. Upon confirmation of proper insertion through the septum of the refill port to achieve a fluidic connection to the drug reservoir of the device 200 (as confirmed visually and/or by pressure readings obtained with a pressure sensor), the refill process is started. Correct insertion may be tested by generating various pressure fluctuations and correlating the pressure changes reported by pressure sensors within the refill system and pressure sensors within the pump. Subsequent steps may be associated with specific pressure thresholds that trigger the end of the current step and the start of the subsequent step. This is illustrated in FIG. 7 (with additional reference to FIG. 6). At an initial time $t_0$, with the system pressure at the steady-state level associated with a full or partially full reservoir and indicated at 701, the vacuum pump 410 is started and the solenoid valve 432 operated to open fluid communication between the pump 410 and the drug reservoir of the device 200 via the needle 102. When the pressure in the drug reservoir (as measured in the reservoir and reported to the refill system, or as measured at the needle 102) reaches the level indicated at 702, the drug reservoir 215 is empty and aspiration is complete. A short interval passes and at the time indicated at 703, the valves 430, 432 are operated to open fluid communication between the pump 415 and the drug reservoir of the device 200 via the fluid line 417' (and the needle 102). The pressure in the receiving reservoir rises as it is filled with washing liquid from the reservoir 220, and when it reaches the level indicated at 704, the reservoir is once again full. The aspiration step is repeated to purge the reservoir of the washing liquid, and another washing cycle (filling followed by vacuum) is performed. After a short time interval following the end of this second washing cycle, the pressure and time reach the values indicated at 706, and the reservoir is filled with drug. That is, the valves 430, 432 are operated to open fluid communication between the pump 415 and the drug reservoir of the device 200 via the fluid line 417 (and the needle 102), and the pressure in the receiving reservoir rises as it is filled with drug from the reservoir 215. The pressure then falls to the steady-state level associated with a full reservoir and indicated at 707. As illustrated in FIG. 8, these curve profiles (i.e., pressure-time relationships) are replicable at various fill and vacuum pressures with the basic pressure-time profile retained. FIG. 9 illustrates the steps of the procedure in flowchart form.

Accordingly, the pressure-time profile shown in FIG. 7 may be used as a template for a normal aspiration and refill sequence. The refill-system controller 225 (FIG. 2) may be programmed to recognize specific parameter (e.g., relative time, duration and/or pressure values, thresholds, curve responses, asymptotic line, inflection points, or other detectable curve characteristics) values and, based on these, initiate or terminate each step of the refill process. In some embodiments, these trigger values are stored permanently in non-volatile memory (e.g., in circuitry 225) following manufacture and calibration. In other embodiments, the values may be modified based on, for example, use and self-assessment by the controller, e.g., via dialog with the operator—that is, the controller may initiate a test procedure and verify proper completion of each step in conformity with the stored trigger values, modifying these values if necessary based on the results of the tests. This is especially useful in embodiments in which the control system is designed for repeated use, and values may drift over time.

The trigger values may be one or more of a detected pressure, flow rate, cumulative flow, pressure slope change, duration of a specific pressure, the time of a change relative to a previous measured value, or plateauing within specific pressure ranges. For example, the inserting, washing, and filling steps may have specific pressure thresholds that signal the end of the step within the sequence.

With reference to FIG. 6, wash solution or new drug is pumped via the fluid line 417, 417' containing a two-way check valve 110, 110' at a pressure greater than the pressure required to open this and any other check valves in the fluid line, or to overcome any internal pressures that may be present in the drug refill portion of the medical device 200. The fill pressure is maintained below a level that would compromise the integrity of the device 200 or open any check valves associated with the drug-delivery portion of the device 200. The fill pressure is also less than the cracking pressure of any check valves associated with the cannula, catheter, or tubing through which the medical device 200 usually pumps drug to the target tissue region. This prevents any inadvertent release of drug or wash solution to the patient. The wash cycle may clean not only the drug chamber but also any filtering mechanisms embedded therein (e.g., built flush with the chamber walls as part of the cannula). This prevents drug aggregate formations, debris, or other material from being released into the patient while allowing the material caught in the filter to be removed and withdrawn during the wash cycle. Other filter configurations including redundant filters partially built into numerous areas of the drug reservoir wall may benefit from washing as discussed herein.

When the drug chamber of the device 200 has been filled with wash solution, a vacuum is drawn through the fluid line 412 containing the one-way valve 112. The pressure in the line 412 is greater than the cracking pressure of the one-way valve 112 but is maintained below a level that would compromise the integrity of the medical device 200 or any check valves and/or tubing sets therein or fluidically connected thereto. This step withdraws the wash solution introduced in the previous step as well as any residual drug contained within the medical device 200.

During the fill cycle, new drug is pumped via the fluid line 417 containing the two-way check valve 110 at a pressure greater than the pressure required to open this and any other check valves in the fluid line, or to overcome any internal pressures that may be present in the drug refill portion of the medical device 200. The fill pressure is maintained below a level that would compromise the integrity of the device 200 or open any check valves associated with the drug-delivery portion of the device 200. The fill pressure is also less than the cracking pressure of any check valves associated with the cannula, catheter, or tubing through which the medical device 200 usually pumps drug to the target tissue region. This prevents inadvertent drug release to the patient during the refill process. However, upon filling the drug reservoir, the clinician may elect to provide a dose. To conserve battery power and drug reservoir space, at the clinician's discretion, the refill pressure may be allowed to rise to overcome the cracking pressure of any check valves associated with the cannula or tubing through which the medical device 200 usually pumps drug to the target tissue region. This allows the clinician to provide a dose of the medication at the time of refill without creating another passage to the target tissue region via a syringe or another cannula. This dose is accurately measured using the refill system's metering capabilities.

When refill is complete, the needle 102 is removed from the refill port of the device 200. Depending on the embodiment, various portions of the refill system may be disposable. In a tethered version, the entire handpiece 100 and tubing may be removed from the base unit and disposed of. Alternatively, if the handpiece 100 is a portable unit with a built-in pumping mechanism, the entire unit may be disposable.

Figure 10:
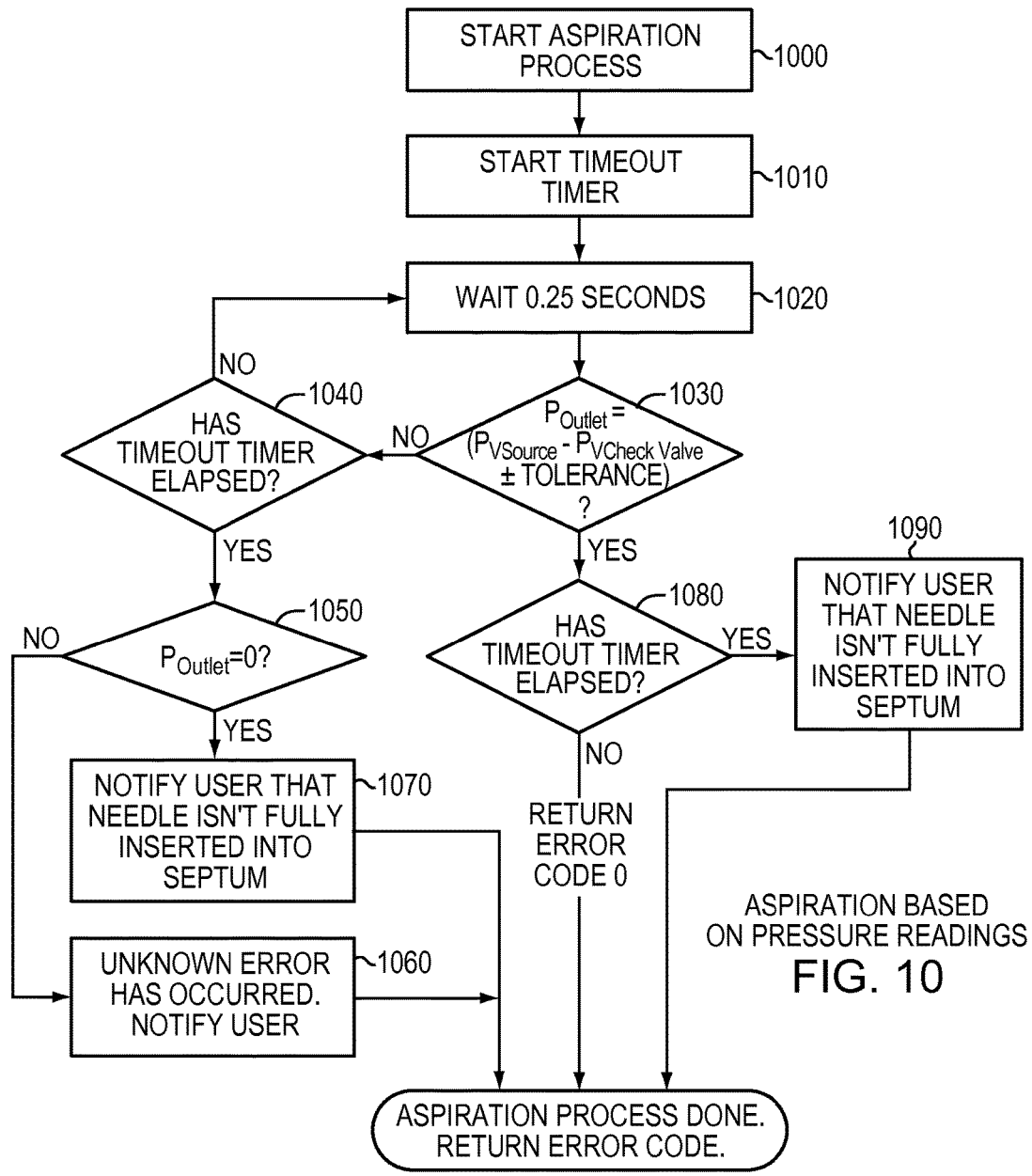
FIG. 10 is a flowchart illustrating the aspiration and fill sequence that generated the graph shown in FIG. 7.

FIG. 10 illustrates an exemplary pressure-comparison decision tree used for aspiration based on pressure readings and a target profile as shown in FIG. 7. The process begins at 1000 and, in a first step 1010, a timeout timer (implemented in control circuitry 225) is activated. Following a delay of 0.25 sec, at step 1030 the outlet pressure $P_{outlet}$ at the tip of the needle 102 is measured and compared to the sum of the vacuum rating of the pump 410 ($P_{VSource}$), the cracking pressure of the check valve 110 ($P_{VCheckvalve}$), and a tolerance value (+/−) selected to account for expected error and/or an acceptable degree of deviation. If the compared values are not equal (step 1030), no action is taken if a timeout value has not been reached, but if sufficient time has passed (step 1040), the outlet pressure is checked to ensure it is not zero (step 1050). If not, an error is registered (step 1060); and if so, the system reports that the needle 102 has not been properly inserted into the drug refill port (step 1070). If, on the other hand, the values compared at step 1030 are equal and sufficient time has elapsed (step 1080) for complete draining of the drug chamber to have occurred, the needle must be blocked due to incorrect insertion (step 1090) which is preventing correct or complete aspiration. But if the values are equal prior to the timeout timer having elapsed, there is a change in $P_{outlet}$ signaling the completion of the aspiration process. The net result of the decision tree is verification of proper traversal of the points 701-703 in FIG. 7. Similar decision trees are used for subsequent steps of the refill process.

Figure 11:
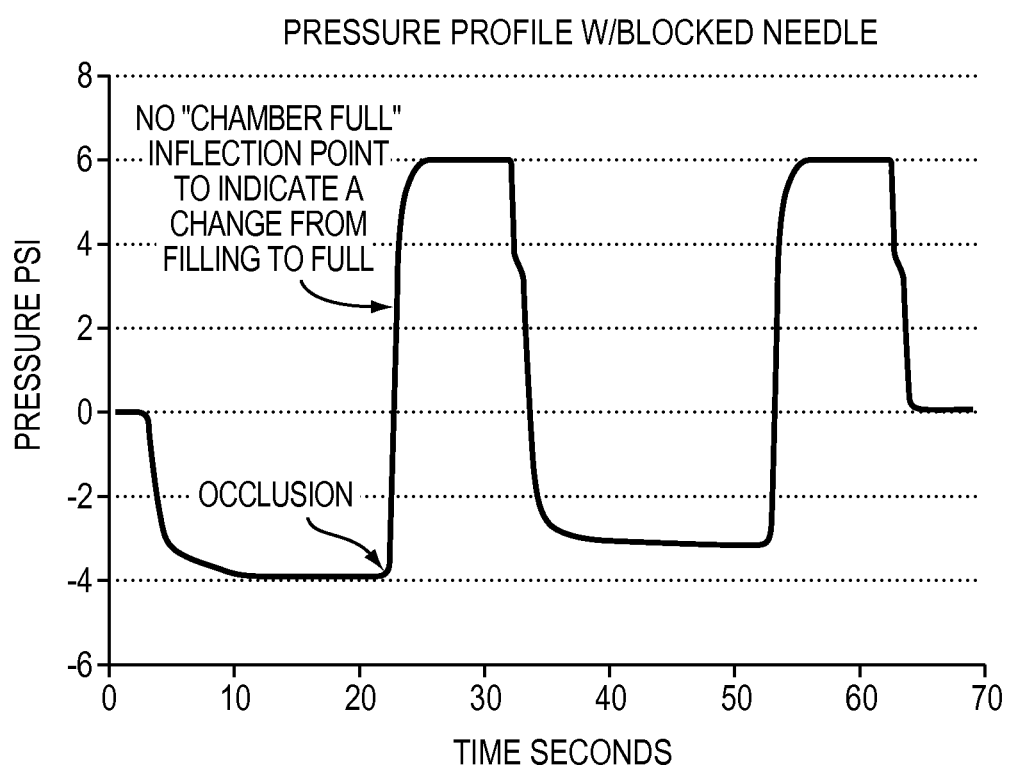
FIG. 11 is a graph illustrating conditions indicative of a blocked needle.

Another mode of error detection is illustrated in FIG. 11. The illustrated pressure profile is similar to those depicted in FIGS. 7 and 8, but deviates in a way that detectably indicates an error—namely, a blocked needle 102. In the normal profile shown in FIG. 7, the pressure plateaus briefly between points 703 and 704, and this plateau occurs when the reservoir is full. Its absence indicates that the increasing pressure is not due to a filling reservoir but to blockage at the needle 102. This condition is computationally detected by comparison of the profile to a template profile having the plateau; although deviations from expected values within defined limits may not indicate an error, the absence of an expected profile feature is far more likely to indicate an error condition.

Electrolysis Refill Step

In drug pump embodiments utilizing an electrolysis actuation mechanism, the electrolysis liquid is also preferably replaced periodically to ensure maintenance of optimal efficiency. Electrolysis solution may be any solution that undergoes at least a partial phase change from a liquid state to a gaseous state upon activation of electrolysis electrodes associated therein. Upon deactivation of the electrolysis electrodes, e.g., in the presence of a catalyst (such as platinum), the evolved gas redissolves in the liquid. The electrolysis solution may consist essentially of a saline solution, a solution comprising magnesium sulfate, sodium sulfate, or any other electrolysis formulation known in the art.

After repeated cycles of electrolysis and recombination, the recombination may become incomplete with some gas not redissolving. As a result, the electrolysis solution does not return to its original liquid-only volume, thereby reducing the effective volume of any adjacent drug chamber on which the electrolysis chamber is operative. Furthermore, one or more electrolysis gases (e.g. hydrogen gas, oxygen gas, etc.) may permeate, resulting in a ratio of gases differing from the original. This may result in a less efficient electrolysis process, requiring greater power to create the same volume of gas and longer electrolytic gas-generation time.

In various embodiments, the refill system described herein may be used to refill the electrolysis chamber of a device 200. With reference to FIG. 2, the handpiece 100 is used to insert the needle 102 into a refill port of the electrolysis chamber. Next, the telemetry wand 232 is employed to interrogate the device 200 and facilitate bi-directional data exchange and/or power transfer. The communication module 230 is used to activate the electrolysis system of the device pump, either using the internal power source of device 200 or by supplying power to the device through wireless telemetry. The electrolysis electrodes are driven to create a predetermined amount of gas within the electrolyte chamber, and at least some of this gas is allowed to escape through the inserted needle 102 (without causing delivery of drug to the patient; the drug chamber may be emptied prior to electrolysis refill as a precaution). For example, the pump 410 may be operated to create a predetermined vacuum to facilitate electrolysis gas removal and shorten gas removal time. The predetermined vacuum is well controlled by the refill system to prevent any damage to the device 200 by continuously monitoring and adjusting vacuum pressure. Continued proper operation and correct insertion of the needle 102 may be continuously or intermittently tested by generating various pressure fluctuations and correlating the pressure changes obtained from pressure sensors within the refill system and the pressure sensors within the electrolysis chamber of the device 200. Finally, the refill system is used to replace the evacuated electrolysis gas with an equivalent amount of fresh electrolyte liquid. A rinse cycle may optionally be employed.

Having described certain embodiments of the invention, it will be apparent to those of ordinary skill in the art that other embodiments incorporating the concepts disclosed herein may be used without departing from the spirit and scope of the invention. For example, various features described with respect to one particular device type and configuration may be implemented in other types of devices and alternative device configurations as well. Accordingly, the described embodiments are to be considered in all respects as only illustrative and not restrictive.

What is claimed is:

1. Apparatus for refilling a reservoir, the apparatus comprising:
 a plurality of reservoirs;
 a plurality of reservoir fluid channels each associated with one of the reservoirs;
 an outlet fluid channel fluidically connected to the reservoir fluid channels;
 a plurality of valves, each having a cracking pressure, for fluidically sealing the reservoir fluid channels and the outlet fluid channel;
 at least one pressure sensor for monitoring pressure in the reservoir fluid channels and the outlet fluid channel;
 at least one actuation mechanism;
 a needle having a lumen in fluid communication with the outlet fluid channel, the needle being configured for insertion into a drug-delivery port of an implantable medical device; and
 a controller for actuating the at least one actuation mechanism and various ones of the valves in accordance with the monitored pressure and a protocol comprising a sequence of steps whereby fluidic pathways are opened between different ones of the reservoirs and the needle in a washing and filling sequence, each of the steps being associated with an expected pressure level.

2. The apparatus of claim 1, wherein the controller is configured to execute a step in the sequence upon detection, via the sensor, of the expected pressure level.

3. The apparatus of claim 1, wherein at least some of the valves are active valves.

4. The apparatus of claim 1, wherein at least some of the valves are passive valves.

5. The apparatus of claim 1, further comprising at least one flow sensor.

6. The apparatus of claim 1, further comprising at least one biosensor.

7. The apparatus of claim 1, wherein the controller is configured to control the actuation mechanism so as to maintain a pressure through the outlet fluid channel below a pressure causing damage to an implantable device connected to the needle.

8. The apparatus of claim 1, wherein the controller is configured to control the actuation mechanism so as to maintain a pressure through the outlet fluid channel below a pressure causing an implantable device connected to the needle to expel material.

9. The apparatus of claim 7, wherein the controller is configured to control the actuation mechanism so as to maintain, during a filling or aspiration step, a pressure through the outlet fluid channel above the cracking pressure of each one of the check valves in each one of the reservoir fluid channels operatively used during the filling or aspiration step.

10. The apparatus of claim 1, wherein the controller (i) comprises a memory for storing a plurality of expected pressure levels and expected intervals therebetween and (ii) is configured to monitor the at least one pressure sensor and, upon detection of an expected pressure level following an expected interval, to initiate or terminate a protocol step.

11. The apparatus of claim 1 further comprising at least one sensor for a parameter other than pressure, wherein the controller (i) comprises a memory for storing a temporal profile of expected parameter values including pressure values and (ii) is configured to monitor the sensors and, upon detection of a deviation from the stored profile, report an error condition.

12. The apparatus of claim 11, wherein the parameter values comprise at least one of a detected flow rate, cumulative flow, pressure slope change, duration of a specific pressure, or plateauing within specific pressure ranges.

13. A method of refilling an implantable device having a drug chamber, the method comprising the steps of:
providing a refill apparatus comprising at least one pump, a plurality of reservoirs, a plurality of reservoir fluid channels each associated with one of the reservoirs, a plurality of valves, each having a cracking pressure, for fluidically sealing the reservoir fluid channels and an outlet fluid channel, the outlet fluid channel fluidically connected to the reservoir fluid channels, and a needle having a lumen in fluid communication with the outlet fluid channel;
monitoring a pressure level;
inserting the needle into a drug-delivery port of the implantable device; and
actuating at least one said pump and various ones of the valves in accordance with the monitored pressure level and a protocol comprising a sequence of steps whereby fluidic pathways are opened between different ones of the reservoirs and the needle in a washing and filling sequence, each of the steps being associated with an expected pressure level.

14. The method of claim 13, wherein the washing and filling sequence comprises flushing a drug chamber of the implantable device by (i) causing a first fluid from a first one of the reservoirs to enter the drug chamber via the needle at a pressure not exceeding a specific pressure threshold, (ii) removing the first fluid from the drug chamber, and (iii) causing a drug-containing liquid to enter at a pressure not exceeding the specific pressure threshold.

15. The method of claim 14, wherein the specific pressure threshold is less than a pressure causing damage to the implantable device.

16. The method of claim 14, wherein the specific pressure threshold is less than a pressure causing flow through the implantable device.

17. The method of claim 13, further comprising the step of monitoring at least one parameter other than pressure and, upon detection of a parameter value matching a stored trigger value, initiating or terminating a step in the sequence.

18. The method of claim 17, wherein the trigger values comprise or consist of at least one of a detected flow rate, cumulative flow, pressure slope change, duration of a specific pressure, or plateauing within specific pressure ranges.

19. The method of claim 13 further comprising monitoring at least one parameter other than and in addition to pressure, and further comprising the steps of:
storing a temporal profile of expected parameter values including pressure values; and
based on the monitored parameters, reporting an error condition upon detection of a deviation from the stored profile.

* * * * *